US00PP10112P

United States Patent [19]

Winchel

[11] Patent Number: Plant 10,112

[45] Date of Patent: Nov. 11, 1997

[54] HYBRID TEA ROSE PLANT VARIETY NAMED 'DONNA DARLIN'

[75] Inventor: Joseph F. Winchel, Harbor City, Calif.

[73] Assignee: Coiner Nursery, LaVerne, Calif.

[21] Appl. No.: 192,657

[22] Filed: Feb. 7, 1994

[51] Int. Cl.[6] ..... A01H 5/00

[52] U.S. Cl. ..... Plt./11

[58] Field of Search ..... Plt./11, 12

*Primary Examiner*—Howard J. Locker

*Attorney, Agent, or Firm*—Christie, Parker & Hale, LLP

[57] ABSTRACT

A new rose variety of the Hybrid Tea class characterized by a distinctive coloring of iridescent red fading to a pale yellow, on a vigorous, disease resistant bush with lush green foliage.

2 Drawing Sheets

BACKGROUND OF THE INVENTION

The present invention relates to a new and distinctive variety of rose plant of the Hybrid Tea class, which was originated by crossing "an unnamed seedling and 'Double Delight'", U.S. Plant Pat. No. 3,847.

SUMMARY OF THE INVENTION

Among the novel characteristics possessed by the new variety which distinguish it from its parents and all other varieties of which I am aware of are;

(1) A deep coloring of the bloom, (2) A vigorous upright plant, and (3) Disease resistance.

Asexual reproduction of the new rose variety by budding, as performed at Wasco, Calif. shows that the aforementioned characteristics and distinctions come true to form and are established and transmitted through succeeding propagations.

COMPARISON WITH PARENT

The new variety differs from its parent, 'Double Delight' in flower coloration as can be seen in the accompanying illustrations.

BRIEF DESCRIPTION OF ILLUSTRATIONS

The accompanying illustrations show typical specimens of the vegetative growth and flowers of the new variety in different stages of development and as depicted in color as nearly true as it is reasonably possible to make in color illustrations of this character.

More specifically: FIG. 1 shows a fully open bloom, a bud just after opening of the sepals, foliage, stem with thorns, and reproductive organs;

FIG. 2 shows a fully open bloom, a flower in the course of opening (obverse), foliage, stem with thorns, and reproductive organs; and FIG. 3 shows a fully open bloom, a side view of a bloom in the course of opening, foliage, stem with thorns, and reproductive organs.

DETAILED DESCRIPTION

Figure 2:
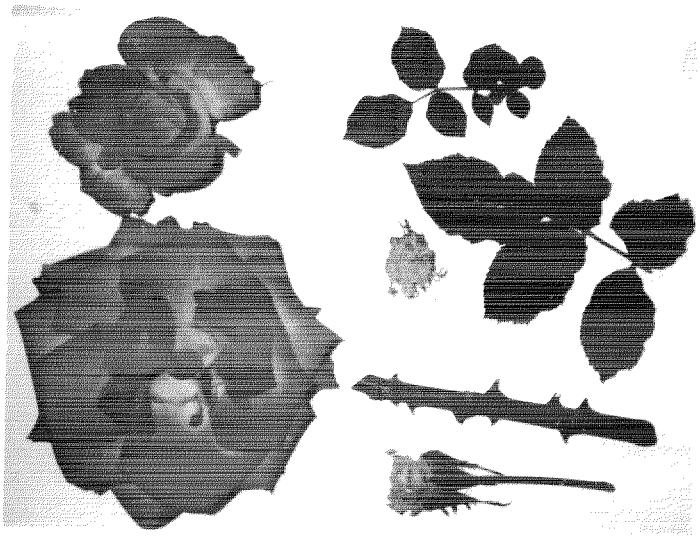
Figure 1:
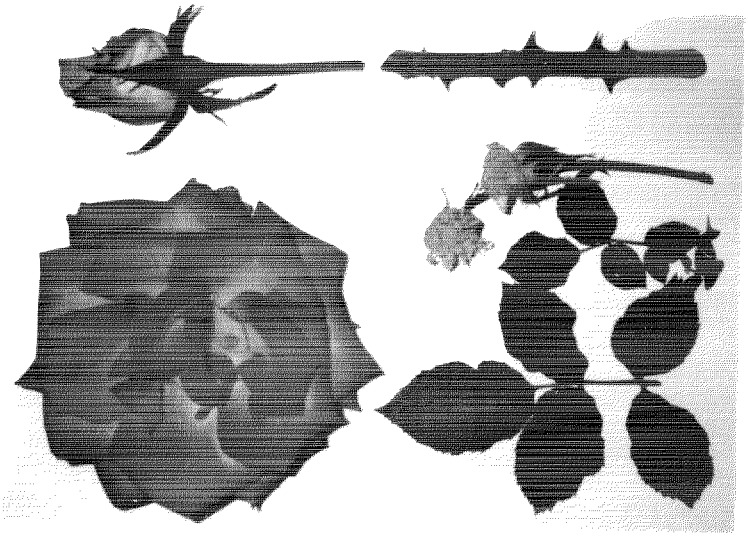
Figure 3:
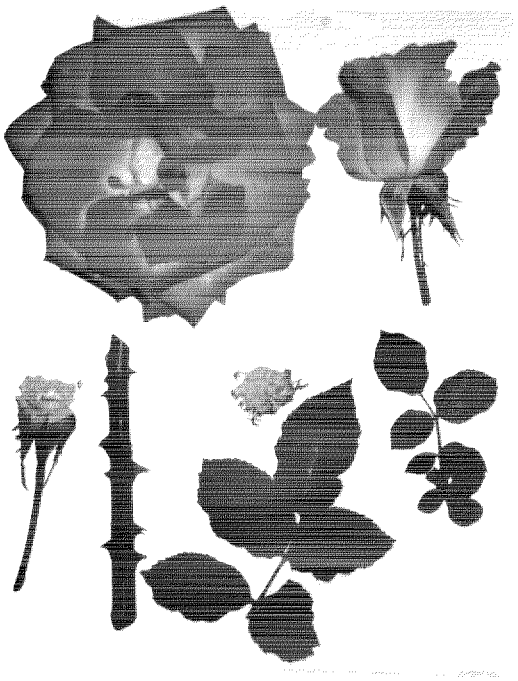

The following is a detailed description of the new variety, with color terminology in accordance with *The Royal Horticultural Society Colour Chart.* The terminology used in the color description herein refers to plate numbers in the aforementioned color chart, e.g. "155A" is plate "155A" of *The Royal Horticultural Society Colour Chart.*

American Rose Society Registration commerial appellation: 'Donna Darlin'
IRAR Appellation: 'WINDON'
Parentage: Seedling.
*Cross.*—an unnamed seedling × "Double Delight".
Class: Hybrid Tea.

The following observations are made of specimens grown outdoors in Kern County, Calif., in the month of November.

FLOWER

Blooming habit:

A: *Bud.*—(1) Size; Medium, usually about 1.5 to 2.5 cm when first formed to about 5 to 6 cm before opening. (2) Form; Pointed with high center. (3) Sepals; Usually 2.5–4.5 cm with normal extension, slight serration with no consistant number of appendages. Color, close to 141C. (4) Peduncle; 9–10 cm, very strong and erect. Color close to 178A, smooth surface. (5) Color when sepals first divide close to 15A. Bud — green close to 141C.

B: *Bloom.*—(1) Size; About 9.5 cm in diameter. Usual depth of bloom from tip of fully opened bloom to tip of hip is 10 cm. Petals are wider than long (Usually about 3.0 cm × 2 cm). (2) Borne; One to the stem. (3) Form; Full and high-centered at first — with petal tightly rolled outward, becoming open and high-centered at maturity. (4) Petalage; Usually 38. (5) Color; A true bi-color with darker edges of near 46A fading to pale yellow near 5A toward the flower center. The underside of the petals are near 46A, but exhibit more light pink tonality, near 62D, and finish to a very pale yellow, near 5A.

C: *Petals.*—(1) Texture; Smooth, even. (2) Form; Ovoid. (3) Arrangement; Regular at all stages. (4) Petaloids; None. (5) Fragrance; Very slight. (6) Lasting quality of the bloom is exceptional on the plant; bloom last about 6 to 8 days on plants grown in La Verne, Calif., during moderate spring weather conditions of warm afternoons and mild evenings. As a cut flower, blooms last for about 7 to 10 days.

REPRODUCTIVE ORGANS

A: Stamen:

(1) *Arrangement.*—Around pistil.

(2) *Number.*—Average, close to 100.

(3) *Length.*—About 1.5 cm.
(4) *Filament.*—About 1.25 cm and close to 169C.
(5) *Anthers.*—07 cm, color 39B fading to 39C.
(6) *Pollen.*—Normal amount, yellow.

B: Pistil:
(1) *Styles.*—About 1 mm, color close to 17A to 17C, yellow. Number close to 148.
(2) *Stigma.*—Color close to 22A.
(3) *Ovary.*—Round.
(4) *Average height.*—1.35 cm.

C: Hips: Will accept pollen.
(1) *Shape.*—Round.
(2) *Color.*—Orange when ripe, color close to 172C.
(3) *Seeds.*—10–15.

PLANT

A: Form: Upright, usually over 4 ft in California climate.
B: Growth: Vigorous.
C: Foliage:
(1) *Size.*—Medium.
(2) *Quantity.*—Average, 5 to 7 leaflets.
(3) *Color.*—New foliage, red — color close to 59A.

Mature foliage is deep green, color close to 135B on the upper surface, and near 135C-D on the lower surface.
(4) *Shape.*—Oval with pointed center.
(5) *Texture.*—Glossy.
(6) *Edge.*—Serrated.

D: Wood:
(1) *New wood.*—Color close to 178A.
(2) *Mature wood.*—Color close to 146B.

E: Thorns:
(1) *Color.*—Close to 160D. Average amount per cane.

F: Resistance to disease:
(1) *Mildew.*—Good.
(2) *Rust.*—Good.
(3) *Black spot.*—Good.

G: Winter hardiness: Average.

I claim:

1. A new and distinctive variety of rose plant of the Hybrid Tea class, substantially as herein shown and described.

* * * * *

UNITED STATES PATENT AND TRADEMARK OFFICE

CERTIFICATE OF CORRECTION

PATENT NO. : Plant 10,112
DATED : November 11, 1997
INVENTOR(S) : Joseph F. Winchel It is certified that error appears in the above-indentified patent and that said Letters Patent is hereby corrected as shown below:

Column 2, line 42, change "bloom" to -- blooms --.
Column 3, line 3, change "07" to -- 0.07 --.

Signed and Sealed this

Fifth Day of May, 1998

*Attest:*

*Attesting Officer*

BRUCE LEHMAN

*Commissioner of Patents and Trademarks*